US011241239B2

(12) United States Patent
Cao et al.

(10) Patent No.: US 11,241,239 B2
(45) Date of Patent: Feb. 8, 2022

(54) OCCLUSIVE MEDICAL DEVICE WITH CHARGED POLYMER COATING

(71) Applicant: BOSTON SCIENTIFIC SCIMED, INC., Maple Grove, MN (US)

(72) Inventors: Hong Cao, Maple Grove, MN (US); Dongming Hou, Plymouth, MN (US); Hongxia Zeng, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 234 days.

(21) Appl. No.: 16/413,090

(22) Filed: May 15, 2019

(65) Prior Publication Data

US 2019/0350591 A1 Nov. 21, 2019

Related U.S. Application Data

(60) Provisional application No. 62/671,549, filed on May 15, 2018.

(51) Int. Cl.
| | | |
|---|---|---|
| *A61B 17/12* | (2006.01) | |
| *A61L 31/10* | (2006.01) | |
| *A61L 33/06* | (2006.01) | |
| *A61B 17/00* | (2006.01) | |

(52) U.S. Cl.
CPC .. *A61B 17/12177* (2013.01); *A61B 17/12122* (2013.01); *A61B 17/12172* (2013.01); *A61L 31/10* (2013.01); *A61L 33/068* (2013.01); *A61B 2017/00632* (2013.01)

(58) Field of Classification Search
CPC ...... A61B 17/0057; A61B 2017/00592; A61B 2017/12172; A61B 2017/00575–00676; A61B 17/12022–12195; A61B 2017/1205–12127
See application file for complete search history.

(56) References Cited

U.S. PATENT DOCUMENTS

| | | | |
|---|---|---|---|
| 1,782,830 | A | 6/1876 | French |
| 1,967,318 | A | 10/1931 | Monahan |
| 3,402,710 | A | 9/1968 | Paleschuck |

(Continued)

FOREIGN PATENT DOCUMENTS

| | | |
|---|---|---|
| CN | 106859722 A | 6/2017 |
| EP | 2872051 A1 | 5/2015 |

(Continued)

OTHER PUBLICATIONS

PCT Search Report from co-pending Application PCT/US02/33808 dated May 20, 2003.

(Continued)

*Primary Examiner* — Darwin P Erezo
*Assistant Examiner* — Brigid K Byrd
(74) *Attorney, Agent, or Firm* — Seager, Tufte & Wickhem LLP

(57) ABSTRACT

An occlusive implant includes an expandable framework that is configured to shift between a collapsed configuration and an expanded configuration. An occlusive member is disposed along at least a portion of the expandable framework. At least part of the occlusive implant is configured to repel fibrinogen. In some cases, the occlusive implant may be configured for placement within a left atrial appendage (LAA) of a patient's heart.

20 Claims, 9 Drawing Sheets

(56) References Cited

U.S. PATENT DOCUMENTS

| | | |
|---|---|---|
| 3,540,431 A | 11/1970 | Mobin-Uddin |
| 3,638,652 A | 2/1972 | Kelley |
| 3,844,302 A | 10/1974 | Klein |
| 3,874,388 A | 4/1975 | King |
| 4,007,743 A | 2/1977 | Blake |
| 4,309,776 A | 1/1982 | Berguer |
| 4,341,218 A | 7/1982 | U |
| 4,364,392 A | 12/1982 | Strother et al. |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,793,348 A | 12/1988 | Palmaz |
| 4,832,055 A | 5/1989 | Palestrant |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,420 A | 4/1992 | Marks |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,883 A | 5/1998 | Halperin |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,810,874 A | 9/1998 | Lefebrve |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,843,118 A | 12/1998 | Sepetka et al. |
| 5,846,260 A | 12/1998 | Maahs |
| 5,846,261 A | 12/1998 | Kotula et al. |
| 5,849,005 A | 12/1998 | Garrison |
| 5,851,232 A | 12/1998 | Lois |
| 5,853,422 A | 12/1998 | Huebsch et al. |
| 5,855,597 A | 1/1999 | Jayaraman |
| 5,865,802 A | 1/1999 | Yoon et al. |
| 5,865,791 A | 2/1999 | Whayne et al. |
| 5,868,708 A | 2/1999 | Hart et al. |
| 5,876,367 A | 3/1999 | Kaganov et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |

(56) References Cited

U.S. PATENT DOCUMENTS

| | | | |
|---|---|---|---|
| 6,010,522 A | 1/2000 | Barbut et al. |
| 6,013,093 A | 1/2000 | Nott et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,096,053 A | 8/2000 | Bates |
| 6,110,243 A | 8/2000 | Wnenchak et al. |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,156,055 A | 12/2000 | Ravenscroft |
| 6,161,543 A | 12/2000 | Cox et al. |
| 6,171,329 B1 | 1/2001 | Shaw et al. |
| 6,179,859 B1 | 1/2001 | Bates et al. |
| 6,214,029 B1 | 4/2001 | Thill et al. |
| 6,231,561 B1 | 5/2001 | Frazier et al. |
| 6,231,589 B1 | 5/2001 | Wessman et al. |
| 6,251,122 B1 | 6/2001 | Tsukernik |
| 6,258,115 B1 | 7/2001 | Dubrul |
| 6,270,490 B1 | 8/2001 | Hahnen |
| 6,277,138 B1 | 8/2001 | Levinson et al. |
| 6,290,674 B1 | 9/2001 | Roue et al. |
| 6,319,251 B1 | 11/2001 | Tu et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,364,895 B1 | 4/2002 | Greenhalgh |
| 6,368,338 B1 | 4/2002 | Knya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,402,746 B1 | 6/2002 | Whayne et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,468,291 B2 | 10/2002 | Bates et al. |
| 6,511,496 B1 | 1/2003 | Huter et al. |
| 6,517,573 B1 | 2/2003 | Pollock et al. |
| 6,547,760 B1 | 4/2003 | Samson et al. |
| 6,551,303 B1 | 4/2003 | Van Tassel et al. |
| 6,551,344 B2 | 4/2003 | Thill |
| 6,558,405 B1 | 5/2003 | McInnes |
| 6,562,058 B2 | 5/2003 | Seguin et al. |
| 6,599,308 B2 | 7/2003 | Amplatz |
| 6,652,555 B1 | 11/2003 | VanTassel et al. |
| 6,652,556 B1 | 11/2003 | VanTassel et al. |
| 6,689,150 B1 | 2/2004 | VanTassel et al. |
| 6,730,108 B2 | 5/2004 | Van Tassel et al. |
| 6,837,901 B2 | 1/2005 | Rabkin et al. |
| 6,855,153 B2 | 2/2005 | Saadat |
| 6,949,113 B2 | 9/2005 | Tassel et al. |
| 6,994,092 B2 | 2/2006 | van der Burg et al. |
| 7,011,671 B2 | 3/2006 | Welch |
| 7,044,134 B2 | 5/2006 | Khairkhahan et al. |
| 7,128,073 B1 | 10/2006 | van der Burg et al. |
| 8,409,192 B2 | 4/2013 | Asirvatham et al. |
| 2001/0034537 A1 | 10/2001 | Shaw et al. |
| 2002/0022860 A1 | 2/2002 | Borillo et al. |
| 2002/0035374 A1 | 3/2002 | Borillo et al. |
| 2002/0062133 A1 | 5/2002 | Gilson et al. |
| 2002/0120297 A1* | 8/2002 | Shadduck ........ A61B 17/12145<br>607/2 |
| 2002/0138094 A1 | 9/2002 | Borillo et al. |
| 2002/0138097 A1 | 9/2002 | Ostrovsky et al. |
| 2003/0023266 A1 | 1/2003 | Borillo et al. |
| 2003/0057156 A1 | 3/2003 | Peterson et al. |
| 2003/0073979 A1* | 4/2003 | Naimark ............ A61B 17/205<br>604/891.1 |
| 2003/0181942 A1 | 9/2003 | Sutton et al. |
| 2003/0220667 A1 | 11/2003 | van der Burg et al. |
| 2004/0098031 A1 | 5/2004 | van der Burg et al. |
| 2004/0215230 A1 | 10/2004 | Frazier et al. |
| 2005/0004652 A1 | 1/2005 | van der Burg et al. |
| 2005/0113861 A1 | 5/2005 | Corcoran et al. |
| 2005/0203568 A1 | 9/2005 | Burg et al. |
| 2005/0287111 A1* | 12/2005 | Schlenoff ............. A61L 29/085<br>424/78.3 |
| 2007/0248640 A1* | 10/2007 | Karabey .......... A61B 17/12172<br>424/423 |
| 2007/0276435 A1 | 11/2007 | Yassinzadeh et al. |
| 2009/0275974 A1* | 11/2009 | Marchand ........ A61B 17/1219<br>606/194 |
| 2012/0312737 A1* | 12/2012 | Miller .................... B01D 71/10<br>210/500.25 |
| 2014/0018841 A1* | 1/2014 | Peiffer ............. A61B 17/12172<br>606/200 |
| 2014/0100596 A1 | 4/2014 | Rudman et al. |
| 2015/0196300 A1* | 7/2015 | Tischler ........... A61B 17/12122<br>606/191 |
| 2015/0342581 A1* | 12/2015 | Mylonakis .............. A61L 31/06<br>606/214 |
| 2016/0106437 A1 | 4/2016 | Van Der Burg et al. |
| 2016/0151105 A1* | 6/2016 | Asirvatham ........... A61B 18/10<br>606/34 |

FOREIGN PATENT DOCUMENTS

| | | |
|---|---|---|
| WO | 9313712 A1 | 7/1993 |
| WO | 9640356 A1 | 12/1996 |
| WO | 9721402 A1 | 6/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9907289 A1 | 2/1999 |
| WO | 9908607 A1 | 2/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0115629 A1 | 3/2001 |
| WO | 0121247 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A2 | 3/2002 |
| WO | 03032818 A2 | 4/2003 |
| WO | 2009052432 A2 | 4/2009 |
| WO | 2017066197 A1 | 4/2017 |
| WO | 2018187732 A1 | 10/2018 |

OTHER PUBLICATIONS

PCT Search Report from PCT/US99/26325 dated Feb. 15, 2000.

Cragg et al; "Nonsurgical Placement of Arterial Endoprosthesis: A New Technique Using Nitinol Wire," Radiology vol. 147, No. 1 pp. 261-263, Apr. 1983.

Cragg et al; "A New Percutaneous Vena Cava Filter", ALJ, 141: 601-604, Sep. 1983.

(56) References Cited

OTHER PUBLICATIONS

Sugita et al; "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.
Ruittenberg, Nonsurgical Therapy of Cardiac Disorders, Pediatric Consult, vol. 5, No. 2, pages not numbered, 1986.
Rashkind et al; "Nonsurgical Closure of Patent Ductus Arteriosus: Clinical Application of the Rashkind PDA Occluder System," Circulation 75, No. 3, 583-592-1987.
Lock et al; "Transcatheter Umbrella Closure of Congenital Heart Defects," Circulation, vol. 75, No. 3, 593-599, 1987.
Lock et al; "Transcatheter Closure of Artrial Septal Defects," Circulation, vol. 79, No. 5 1091-1099, May 1989.
Wessel et al; "Outpatient Closure of the Patent Ductus Arteriosus," Circulation, vol. 77, No. 5 1068-1071, 1988.
Lim et al, "Concurrent Application of Charge Using a Novel Circuit Prevents Heat-Related Coagulum Formation During Radiofrequency Ablation", JCE, 19, pp. 843-850, 2008.
Padolecchia et al, "Role of Electrothrombosis in Anurysm Treatment with Gugliemi Detachable Coils: An In Vitro Scanning Electron Microscopic Study", AJNR, 22, pp. 1757-1760, 2001.
Sit et al, "Surface-Dependent Conformations of Human Fibrinogen Observed by Atomic Force Microscopy under Aqueous Conditions", Thromb Haemost, 82, pp. 1757-1760, 2001.
Srinivasan et al; "Role of Surface Charge of the Blood Vessel Wall, Blood Cells, and Prosthetic Materials in Intravascular Thrombosis", J. Colloid & Interface Science , vol. 32, 3: pp. 456-463, 1970.
Fresnais et al; "Poly(acrylic acid)-Coated Iron Oxide Nanoparticles: Quantitative Evaluation of the Coating Properties and Applications for the Removal of a Pollutant Dye", Journal of Colloid and Interface Science, 395, pp. 24-30, 2013.
Yunn-Hwa Ma et al; "Magnetically Targeted Thrombolysis with Recombinant Tissue Plasminogen Activator Bound to Polyacrylic Acid-Coated Nanoparticles", Biomaterials, 30, pp. 3343-3351, 2009.
Ueda et al; "Effect of the Structure of Cationic Polysulfone on the Flocculation of Kaolinite", Journal of Applied Polymer Science, vol. 12, pp. 2383-2393, 1968.
Wan et al; "Modification of Polysulfone (PSF) Hollow Fiber Membrane (HFM) with Zwitterionic or Charged Polymers", Ind. Eng. Chem. Res. 56, pp. 7576-7584, 2017.
Horowitz et al. "Does Electrothrombosis Occur Immediately after Embolization of an Aneurysm with Gugliemi Detachable Coils," AJNR, 18, pp. 510-513, 1997.
Invitation to Pay Additional Fees dated Feb. 22, 2019 for International Application No. PCT/US2018/066163.
International Search Report and Written Opinion dated Jul. 22, 2019 for International Application No. PCT/US2019/032464.

\* cited by examiner

OCCLUSIVE MEDICAL DEVICE WITH CHARGED POLYMER COATING

CROSS-REFERENCE TO RELATED APPLICATIONS

This application claims the benefit of priority under 35 U.S.C. § 119 to U.S. Provisional Application Ser. No. 62/671,549, filed May 15, 2018, the entirety of which is incorporated herein by reference.

TECHNICAL FIELD

The present disclosure pertains to occlusive medical devices. More particularly, the present disclosure pertains to occlusive medical devices usable within the left atrial appendage (LAA).

BACKGROUND

The left atrial appendage (LAA) is a small organ attached to the left atrium of the heart as a pouch-like extension. In some cases, such as in patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage.

As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

This disclosure provides design, material, manufacturing method, and use alternatives for occlusive medical devices. An example occlusive implant includes an expandable framework that is configured to shift between a collapsed configuration and an expanded configuration and an occlusive member that is disposed along at least a portion of the expandable framework. At least part of the occlusive implant is adapted to repel and/or attract fibrinogen.

Alternatively or additionally, the occlusive implant has a leading edge, and an area of the occlusive member proximate the leading edge may be treated to repel fibrinogen.

Alternatively or additionally, the expandable framework includes a central structure, and an area of the occlusive member proximate the central structure may be treated to repel fibrinogen.

Alternatively or additionally, at least part of the occlusive implant may be configured to carry a negative charge at neutral pH.

Alternatively or additionally, at least part of the occlusive implant includes a polymer that may be negatively charged at neutral pH.

Alternatively or additionally, the polymer that may be negatively charged at neutral pH covers at least part of the occlusive member.

Alternatively or additionally, the polymer that may be negatively charged at neutral pH may be spray coated onto the occlusive member.

Alternatively or additionally, the polymer that may be negatively charged at neutral pH may be physically blended with a material forming the occlusive member.

Alternatively or additionally, the polymer that may be negatively charged at neutral pH may be provided as a copolymer with a material forming the occlusive member.

Alternatively or additionally, the occlusive member may include a polymeric coating covering at least a portion of the expandable framework, and the polymeric coating may be positively charged at neutral pH in order to attract fibrinogen.

Alternatively or additionally, the occlusive member may be formed of polyethylene terephthalate (PET).

Alternatively or additionally, the expandable framework may include a plurality of anchor members extending radially outward from the expandable framework.

Alternatively or additionally, the expandable framework and the plurality of anchor members may be formed from a unitary tubular member.

Alternatively or additionally, the expandable framework, in the expanded configuration, may be configured to fit into a left atrial appendage (LAA) of a patient's heart.

Alternatively or additionally, a second part of the occlusive implant not configured to repel fibrinogen may be configured to attract fibrinogen.

An example medical implant for occluding a left atrial appendage (LAA) of a patient's heart includes an expandable framework that is configured to shift between a collapsed configuration and an expanded configuration, an occlusive member that extends over and is supported by at least a portion of the expandable framework, and a coating that disposed over at least part of the occlusive member and is configured to repel fibrinogen.

Alternatively or additionally, the coating that is configured to repel fibrinogen may include a polymer that is negatively charged at neutral pH.

Alternatively or additionally, the occlusive implant has a leading edge, and the coating that is configured to repel fibrinogen may extend over the leading edge.

Alternatively or additionally, the expandable framework may include a central structure, and the coating that is configured to repel fibrinogen may extend over the central structure.

Another example medical implant for occluding a left atrial appendage (LAA) of a patient's heart includes an expandable framework that is configured to shift between a collapsed configuration and an expanded configuration and an occlusive member that extends over and supported by at least a portion of the expandable framework. A first coating that is configured to repel fibrinogen is disposed over a first part of the occlusive member and a second coating that is configured to attract fibrinogen is disposed over a second part of the occlusive member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
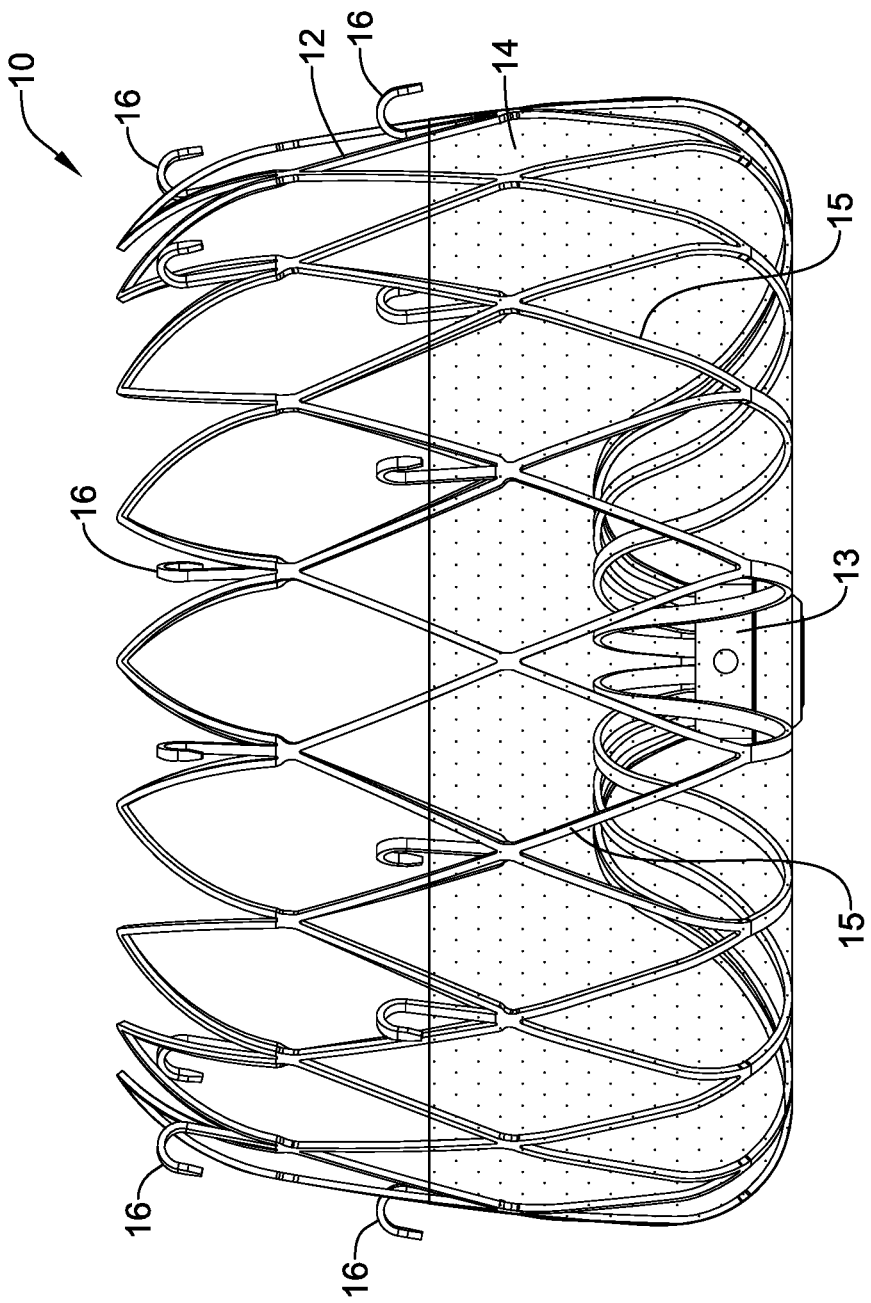
FIG. 1 is a plan view of an example occlusive implant.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. In some cases, fibrinogen circulating within the blood contributes to the formation and growth of thrombi. Example medical devices and/or occlusive implants that close off the left atrial appendage are disclosed herein.

FIG. 1 illustrates an example occlusive implant 10. The implant 10 may include an expandable framework 12. In some cases, the expandable framework 12 includes a central structure 13, where a number of individual elements 15 forming the expandable framework come together. The occlusive implant 10 may also include an occlusive member 14 disposed on, disposed over, disposed about, or covering at least a portion of the expandable framework 12. In some embodiments, the occlusive member 14 may be disposed on, disposed over, disposed about or cover at least a portion of an outer (or outwardly-facing) surface of the expandable framework 12. FIG. 1 further illustrates that the occlusive member 14 may extend only partially along the longitudinal extent of the expandable framework 12. However, this is not intended to be limiting. Rather, the occlusive member 14 may extend along the longitudinal extent of the expandable framework to any degree (e.g., the full longitudinal extend of the expandable framework 12).

In some embodiments, the occlusive member 14 may be permeable or impermeable to blood and/or other fluids, such as water. In some embodiments, the occlusive member 14 may include a woven, braided and/or knitted material, a fiber, a sheet-like material, a fabric, a polymeric membrane, a metallic or polymeric mesh, a porous filter-like material, or other suitable construction. In some cases, the occlusive member 14 may be formed of a polymeric material. A suitable polymeric material is polyethylene terephthalate (PET), which is a thermoplastic polyester. In some embodiments, the occlusive member 14 may prevent thrombi (i.e. blood clots, etc.) from passing through the occlusive member 14 and out of the left atrial appendage into the blood stream. In some embodiments, the occlusive member 14 may promote endothelization after implantation, thereby effectively removing the left atrial appendage from the patient's circulatory system. Some suitable, but non-limiting, examples of materials for the occlusive member 14 are discussed below.

FIG. 1 further illustrates that the expandable framework 12 may include a plurality of anchor members 16 disposed about a periphery of the expandable framework 12. The plurality of anchor members 16 may extend radially outward from the expandable framework 12. In some embodiments, at least some of the plurality of anchor members 16 may each have and/or include a body portion and a tip portion projecting circumferentially therefrom, as shown in FIG. 1. Some suitable, but non-limiting, examples of materials for the expandable framework 12 and/or the plurality of anchor members 16 are discussed below.

In some examples, the expandable framework 12 and the plurality of anchor members 16 may be integrally formed and/or cut from a unitary member. In some embodiments, the expandable framework 12 and the plurality of anchor members 16 may be integrally formed and/or cut from a unitary tubular member and subsequently formed and/or heat set to a desired shape in the expanded configuration. In some embodiments, the expandable framework 12 and the plurality of anchor members 16 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 12 include laser cutting, machining, punching, stamping, electro discharge machining (EDM), chemical dissolution, etc. Other means and/or methods are also contemplated.

As illustrated in FIG. 1, the plurality of anchor members 16 disposed along the expandable framework 12 may include two rows of anchor members 16. However, this is not intended to be limiting. Rather, the expandable framework 12 may include a single row of anchor members 16. In other examples, the expandable framework 12 may include more than two rows of anchor members 16. For example, in some instances the expandable framework 12 may include 1, 2, 3, 4 or more rows of anchor members 16.

Figure 2:
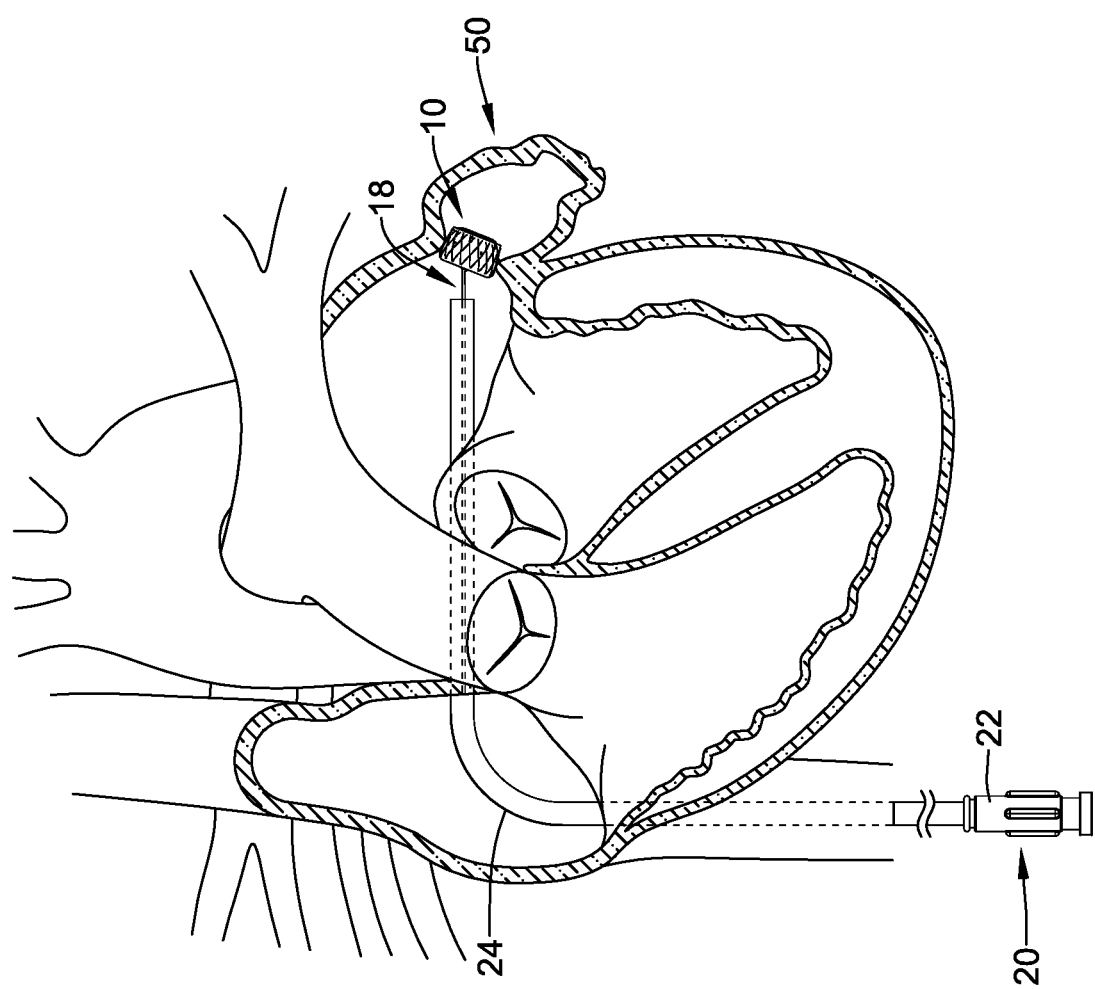
FIG. 2 shows an example occlusive implant positioned in the heart.

FIG. 2 illustrates that the occlusive implant 10 may be inserted and advanced through a body lumen via an occlusive implant delivery system 20. FIG. 2 further illustrates the occlusive implant 10 being delivered and positioned within the left atrial appendage 50. In some instances, an occlusive implant delivery system 20 may include a delivery catheter 24 which is guided toward the left atrium via various chambers and lumens of the heart (e.g., the inferior vena cava, the right atrium, etc.) to a position adjacent the left atrial appendage 50.

The delivery system 20 may include a hub member 22 coupled to a proximal region of the delivery catheter 24. The hub member 22 may be manipulated by a clinician to direct the distal end region of the delivery catheter 24 to a position adjacent the left atrial appendage 50. In some embodiments, an occlusive implant delivery system may include a core wire 18. Further, a proximal end of the expandable framework 12 may be configured to releasably attach, join, couple, engage, or otherwise connect to the distal end of the core wire 18. In some embodiments, an end region of the expandable framework 12 may include a threaded insert coupled thereto. In some embodiments, the threaded insert may be configured to and/or adapted to couple with, join to, mate with, or otherwise engage a threaded member disposed at the distal end of a core wire 18. Other means of releasably coupling and/or engaging the proximal end of the expandable framework 12 to the distal end of the core wire 18 are also contemplated.

Figure 3:
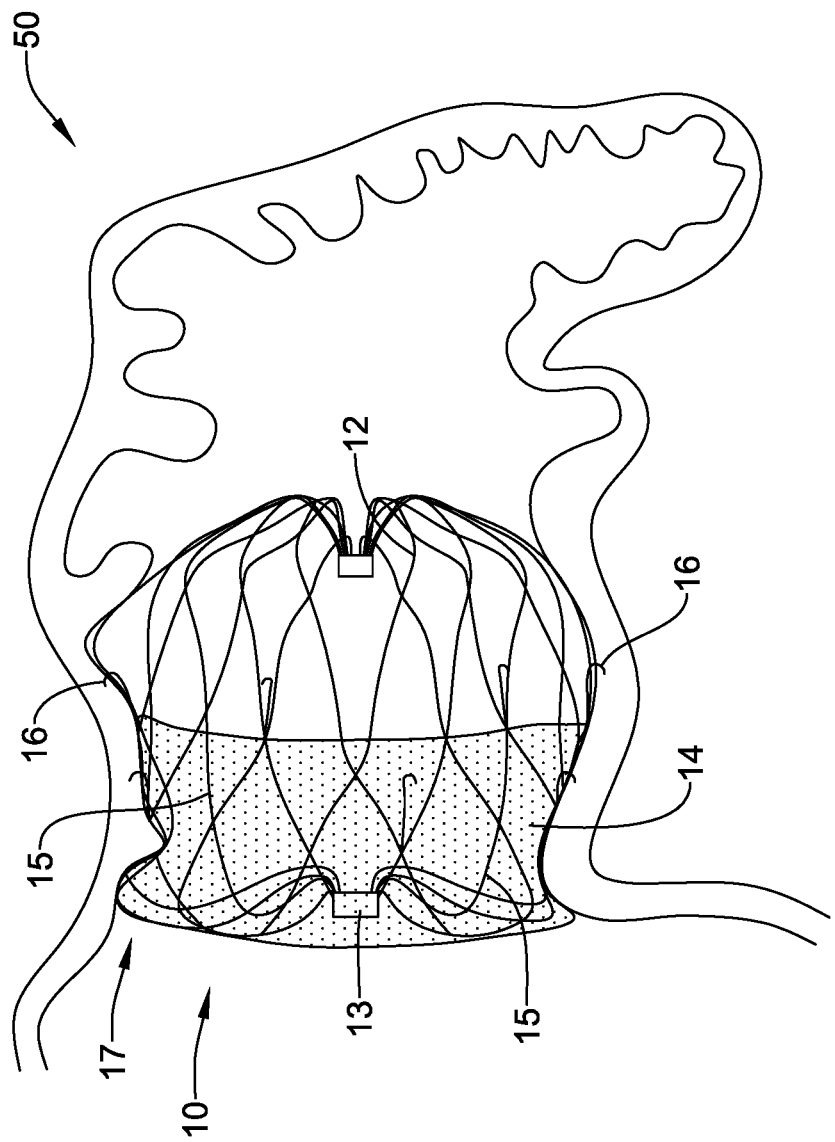
FIG. 3 shows an example occlusive implant positioned in the left atrial appendage.

FIG. 3 illustrates a left atrial appendage occlusive implant 10 positioned adjacent the left atrial appendage 50 via the delivery catheter 24 (described above with respect to FIG. 2). As discussed above, in some examples, the implant 10 may be configured to shift between a collapsed configuration and an expanded configuration. For example, in some instances, the occlusive implant may be in a collapsed configuration during delivery via occlusion implant delivery system, whereby the occlusive implant expands to an expanded configuration once deployed from the occlusion implant delivery system. FIG. 3 also illustrates several regions of the occlusive implant 10 that tend to attract fibrinogen, and thus encourage the growth of thrombi. In some cases, the central structure 13 tends to be a region that attracts fibrinogen, and thus encourages the growth of thrombi. The occlusive implant 10 includes a leading edge 17 that tends to be a region that attracts fibrinogen, and thus encourages the growth of thrombi.

Additionally, FIG. 3 illustrates that the expandable framework 12 may be compliant and, therefore, substantially conform to and/or be in sealing engagement with the shape and/or geometry of a lateral wall of a left atrial appendage in the expanded configuration. In some embodiments, the occlusive implant 10 may expand to a size, extent, or shape less than or different from a maximum unconstrained extent, as determined by the surrounding tissue and/or lateral wall of the left atrial appendage. Additionally, FIG. 3 illustrates that the expandable framework 12 may be held fixed adjacent to the left atrial appendage by one or more anchoring members 16.

Further, it can be appreciated that the elements of the expandable framework 12 may be tailored to increase the flexibility and compliance of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 discussed above to include various features, components and/or configurations which improve the sealing capabilities of the occlusive implant within the left atrial appendage.

Figure 4:
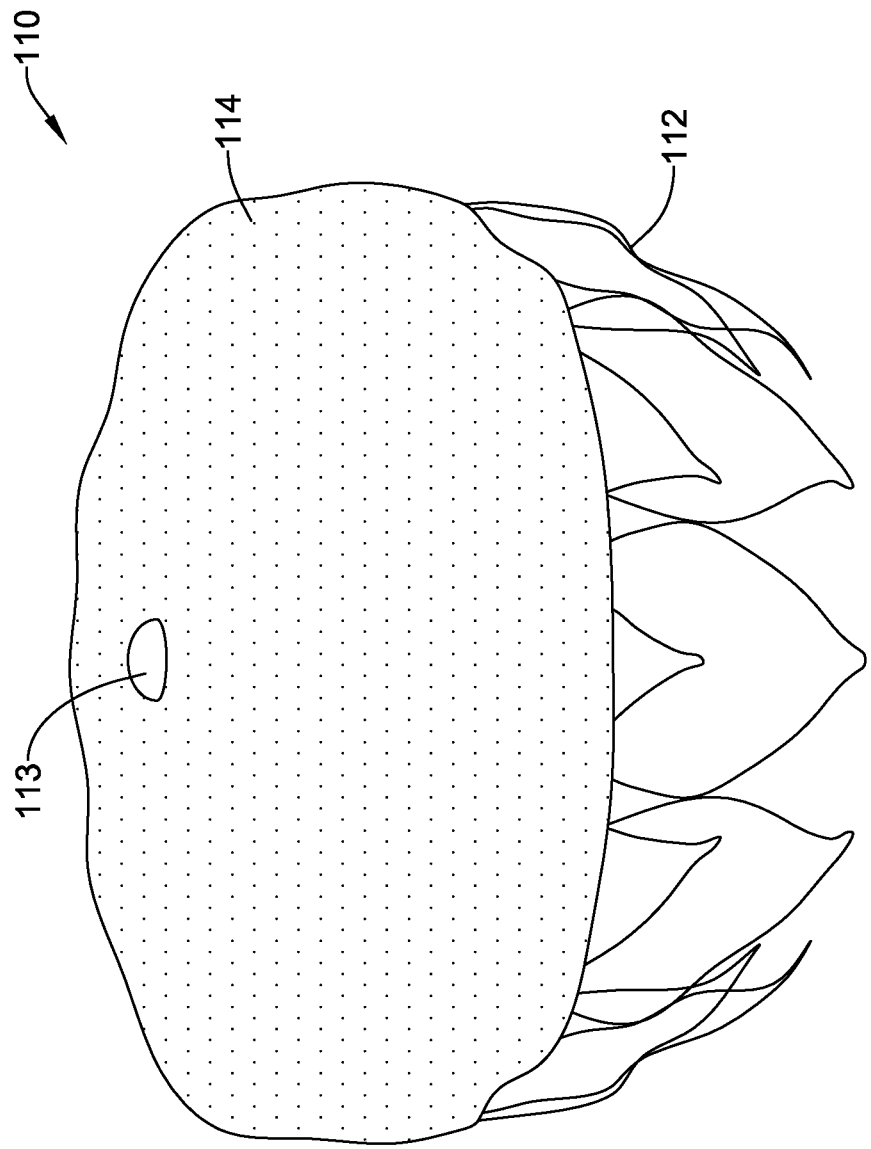
FIG. 4 is a plan view of an example occlusive implant.

In some cases, at least a portion of the occlusive implant 10 may be treated or otherwise configured to selectively repel fibrinogen, in order to selectively reduce the formation of thrombi relative to certain parts of the occlusive implant 10. In some cases, at least a portion of the occlusive implant 10 may be treated or otherwise configured to selectively attract fibrinogen, in order to selectively encourage the formation of thrombi relative to certain parts of the occlusive implant 10. FIG. 4 shows an occlusive implant 110. FIGS. 5 through 8 provide examples of how the occlusive implant 110 may be configured to selectively repel and/or attract fibrinogen.

In FIG. 4, the occlusive implant 110 includes an expandable framework 112. In some cases, the expandable framework 112 includes a central structure 113, where a number of individual elements 15 forming the expandable framework come together. The occlusive implant 110 may also include an occlusive member 114 disposed on, disposed over, disposed about, or covering at least a portion of the expandable framework 112. In some embodiments, the occlusive member 114 may be disposed on, disposed over, disposed about or cover at least a portion of an outer (or outwardly-facing) surface of the expandable framework 112. FIG. 4 further illustrates that the occlusive member 114 may extend only partially along the longitudinal extent of the expandable framework 112. However, this is not intended to be limiting. Rather, the occlusive member 114 may extend along the longitudinal extent of the expandable framework to any degree (e.g., the full longitudinal extend of the expandable framework 112). In some cases, the expandable framework 112 may include various features described with respect to the expandable framework 12 (FIG. 1)

In some embodiments, the occlusive member 114 may be permeable or impermeable to blood and/or other fluids, such as water. In some embodiments, the occlusive member 114 may include a woven, braided and/or knitted material, a fiber, a sheet-like material, a fabric, a polymeric membrane, a metallic or polymeric mesh, a porous filter-like material, or other suitable construction. In some cases, the occlusive member 114 may be formed of a polymeric material. A suitable polymeric material is polyethylene terephthalate (PET), which is a thermoplastic polyester. In some embodiments, the occlusive member 114 may prevent thrombi (i.e. blood clots, etc.) from passing through the occlusive member 114 and out of the left atrial appendage into the blood stream. In some embodiments, the occlusive member 114 may promote endothelization after implantation, thereby effectively removing the left atrial appendage from the patient's circulatory system. Some suitable, but non-limiting, examples of materials for the occlusive member 14 are discussed below.

In some examples, the expandable framework 112 may be integrally formed and/or cut from a unitary member. In some embodiments, the expandable framework 112 may be integrally formed and/or cut from a unitary tubular member and subsequently formed and/or heat set to a desired shape in the expanded configuration. In some embodiments, the expandable framework 112 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 112 include laser cutting, machining, punching, stamping, electro discharge machining (EDM), chemical dissolution, etc. Other means and/or methods are also contemplated.

Figure 5:
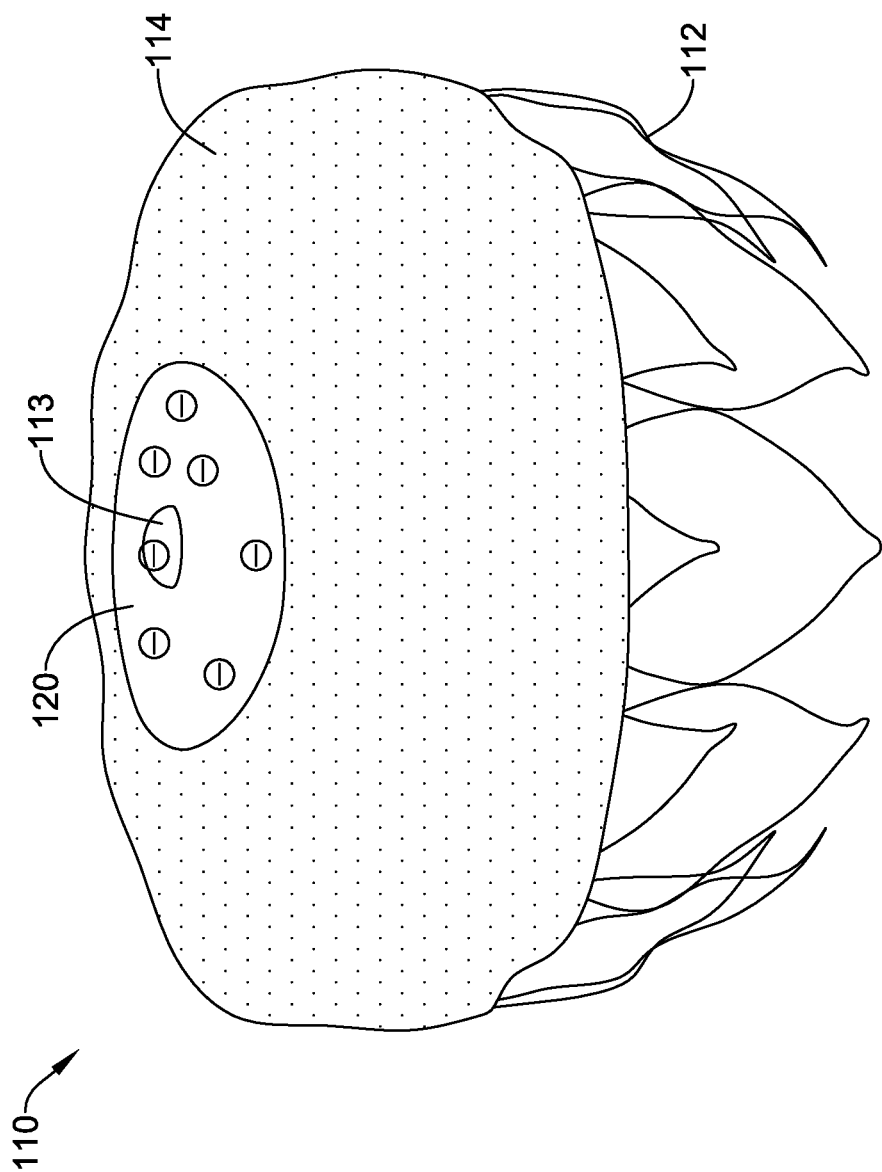
FIG. 5 is a plan view of an example occlusive implant.

In FIG. 5, it can be seen that there is a negatively charged region 120 that is disposed relative to the occlusive member 114, proximate the central structure 113. In some cases, providing a negatively charged region 120 in this area helps to repel fibrinogen, which tend to be negatively charged at neutral pH. It will be appreciated that by repelling fibrinogen in the area around the central structure 113, this can reduce or eliminate the formation of thrombi that would otherwise form in this area. Since the remaining portion of the occlusive member 114 does not include the negatively charged region 120, thrombi and other tissue growth may be permitted. In some cases, the negatively charged region 120 may be formed of a polymer that is negatively charged at neutral pH, such as is found within the blood stream. In this, neutral pH may be defined as ranging from 7.35 and 7.45, which is generally the range within blood pH is maintained by the human body.

In some cases, the negatively charged region 120 may be formed by spraying coating onto the occlusive member 114 a polymer that is negatively charged at neutral pH. In some cases, the polymer may instead be physically mixed into the material forming the occlusive member 114. In some instances, the polymer may instead be formed as a copolymer with the material forming the occlusive member 114. In some cases, for example, the occlusive member 114 may be formed of polyethylene terephthalate (PET). The polymer that is negatively charged at neutral pH may be poly(acrylic acid), carboxymethylcellulose, polystyrene sulfonate, quaternized poly(4-vinyl pyridine) and others. In some cases, a negatively charged surfactant such as a siloxane surfactant may be used.

Figure 6:
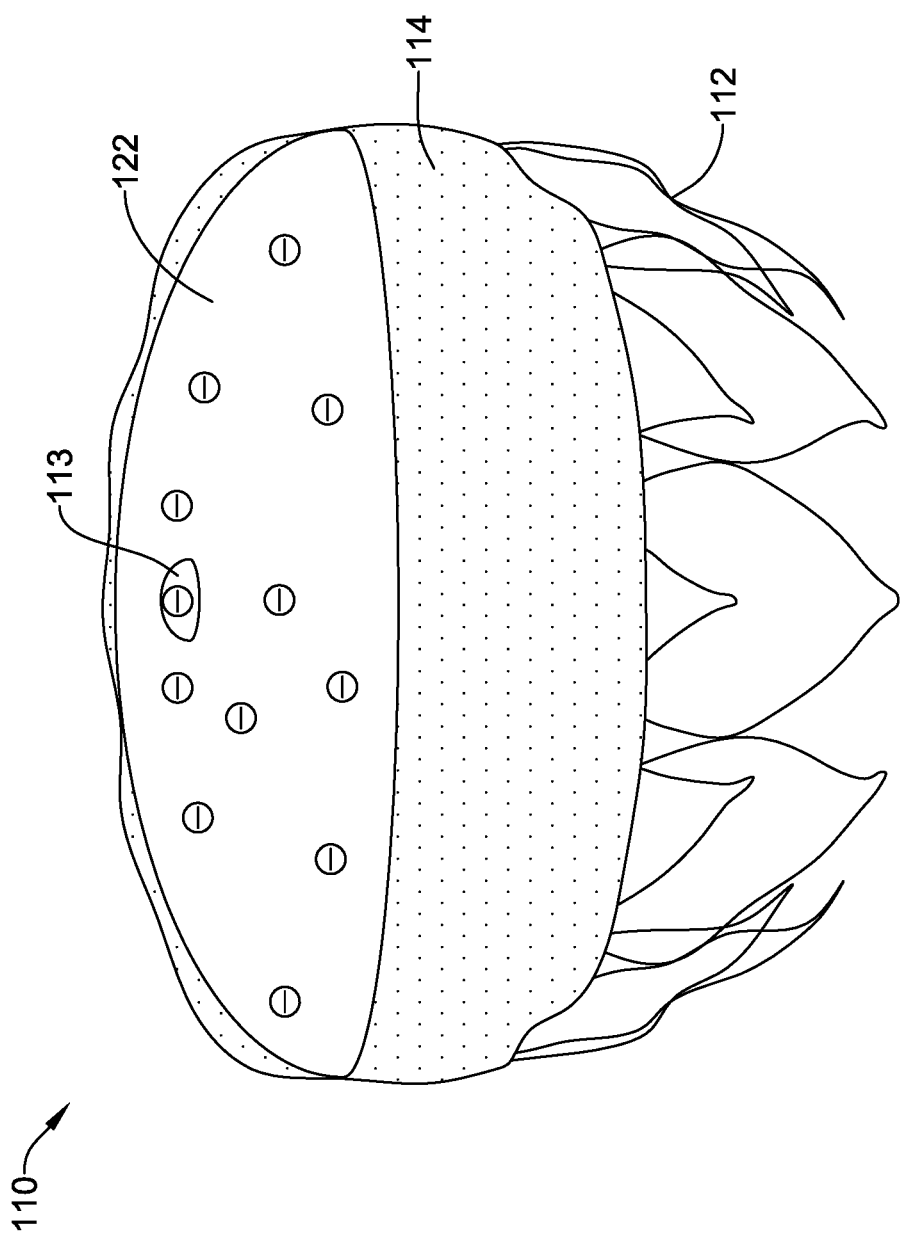
FIG. 6 is a plan view of an example occlusive implant.

In FIG. 6, it can be seen that there is a negatively charged region 122 that is disposed relative to the occlusive member 114 that spans a larger area than the negatively charged region 120 shown in FIG. 5. It will be appreciated that the negatively charged region 122 spans the central structure 113 as well as what would be the leading edge (with reference to the leading edge 17 shown in FIG. 3). In some cases, since the occlusive implant 110 may be considered as being radially symmetrical, and there may not be a good way to dictate its rotational position relative to the left atrial appendage (LAA) 50, shown in FIG. 3, having the negatively charged region 122 sized as shown may mean that the leading edge 17 is covered, regardless of the rotational orientation in which the occlusive implant 110 is implanted.

In some cases, the negatively charged region 122 may be formed by spraying coating onto the occlusive member 114 a polymer that is negatively charged at neutral pH. In some cases, the polymer may instead be physically mixed into the material forming the occlusive member 114. In some instances, the polymer may instead be formed as a copolymer with the material forming the occlusive member 114. In some cases, for example, the occlusive member 114 may be formed of polyethylene terephthalate (PET). The polymer that is negatively charged at neutral pH may be poly(acrylic acid), carboxymethylcellulose, polystyrene sulfonate, quaternized poly(4-vinyl pyridine), and others. In some cases, a negatively charged surfactant such as a siloxane surfactant may be used.

Figure 7:
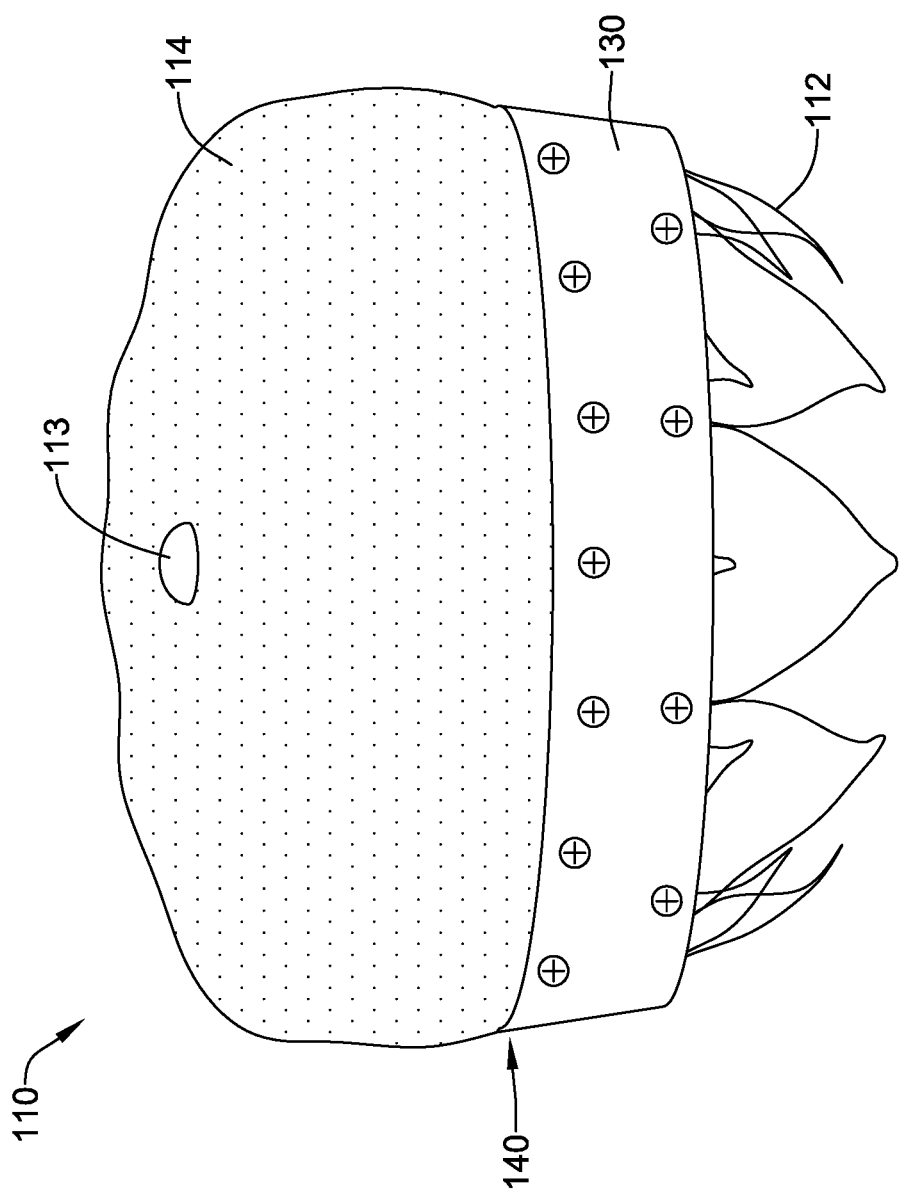
FIG. 7 is a plan view of an example occlusive implant.

In some cases, there may be a desire to encourage the formation of thrombi in particular regions of the occlusive implant 110. In FIG. 7, the occlusive implant 110 includes a positively charged region 130. In some cases, providing a positively charged region 130 in this area helps to attract fibrinogen, which tend to be negatively charged at neutral pH. It will be appreciated that by attracting fibrinogen around a periphery 140 of the occlusive implant 110, this can encourage the formation of thrombi and thus encourage endothelization. In some cases, there is a desire to encourage endothelization that begins around the periphery 140 and extends inwardly.

In some cases, the positively charged region 130 may be formed by spraying coating onto the occlusive member 114 a polymer that is positively charged at neutral pH. In some cases, the polymer may instead be physically mixed into the material forming the occlusive member 114. In some instances, the polymer may instead be formed as a copolymer with the material forming the occlusive member 114. In some cases, for example, the occlusive member 114 may be formed of polyethylene terephthalate (PET). The polymer that is positively charged at neutral pH may be one or more of isopropylacrylamide, polysulfone, silicone, dialkyl quaternary ammonium compounds, poly(DMEMA-b-PDMEMA-Co-BMA-Co-PAA), and the like.

Figure 8:
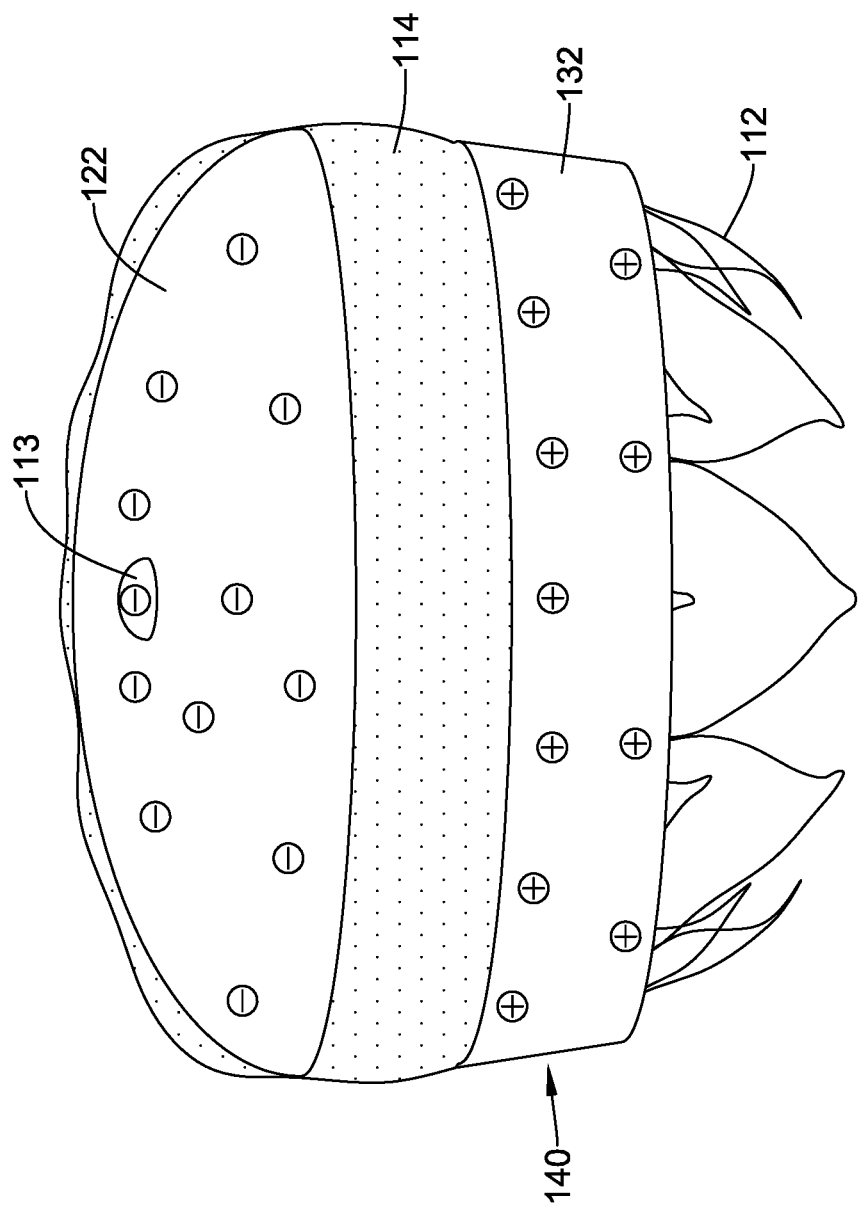
FIG. 8 is a plan view of an example occlusive implant.

In some cases, as shown in FIG. 8, there may be a desire to discourage endothelization on some portions of the occlusive implant 110 and to encourage endothelization on other portions of the occlusive implant 110. In FIG. 8, it can be seen that the occlusive implant 110 includes both a negatively charged region 120 and a positively charged region 130. While the negatively charged region 120 and the positively charged region 130 are both shown as discrete regions, it will be appreciated that in some cases there may be a more gradual gradient in charge, i.e., the negatively charged region 120 may vary from a highly negatively charged portion to a lightly negatively charged portion. The positively charged region 120 may vary from a highly positively charged region to a lightly positively charged portion. These are just examples.

Figure 9:
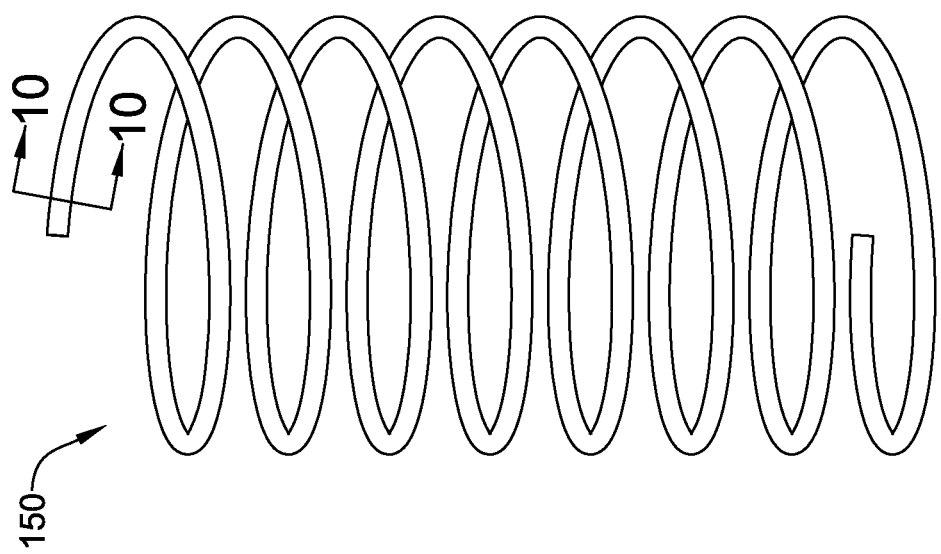
FIG. 9 is a plan view of an example embolization device.

In some cases, an embolization device may include a positively charged polymer to attract fibrinogen. Embolization devices may be used when there is a desire to block blood flow through a particular blood vessel. This may be done, for example, when a particular blood vessel provides blood flow to a tumor, and there is a desire to kill the tumor, or at least reduce its growth. FIG. 9 shows an embolization device 150 that generally takes the shape, in an expanded configuration (as shown) of a coil. As will be appreciated, the embolization device 150 is shown schematically as a coil. In some cases, the embolization device 150 may have a more complicated structure. For example, the embolization device 150 may be formed from a filar or wire that is coiled into a primary coil, which is then shaped into a secondary coil. Further details regarding the structure of the embolization device 150 may be found in U.S. Pat. No. 6,984,240, the disclosure of which is incorporated by reference in its entirety.

Figure 10:
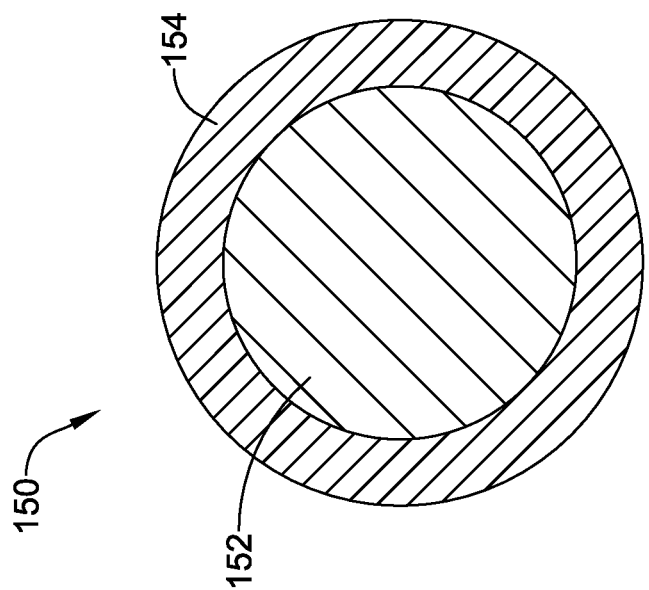
FIG. 10 is a cross-sectional view of the example embolization device taken along line 10-10 of FIG. 9.

As can be seen by the cross-section shown in FIG. 10, the embolization device 150 may include a central member 152 that is coated with a positively charged polymer 154. In some cases, the positively charged polymer 154, which may be thought of as being positively charged at neutral pH, may function as an occlusive member by attracting fibrinogen. Illustrative but non-limiting examples of materials that may be used in forming the central member 152 include metals such as platinum, stainless steel, zinc, nickel, cobalt, aluminum and aluminum alloys, and Nitinol®. Illustrative but non-limiting examples of polymers that are positively charged at neutral pH and that may be used are isopropylacrylamide, polysulfone, silicone, dialkyl quaternary ammonium compounds, block polymers such as poly (DMEMA-b-PDMEMA-Co-BMA-Co-PAA) and the like.

The materials that can be used for the various components of the medical devices disclosed herein may include those commonly associated with medical devices. However, this is not intended to limit the devices and methods described herein, as the discussion may be applied to other components of the occlusive implants 10, 110 disclosed herein.

The occlusive implants 10, 110 or portions thereof, as well as the embolization device 150, may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the occlusive implants 10, 110 and/or the embolization device 150 may also be doped with, made of, or otherwise include a radiopaque material. Radiopaque materials are understood to be materials capable of producing a relatively bright image on a fluoroscopy screen or another imaging technique during a medical procedure. This relatively bright image aids the user in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MRI) compatibility is imparted into the occlusive implants 10, 110 and/or the embolization device 150. For example, the occlusive implants 10, 110 and/or the embolization device 150 may include a material that does not substantially distort the image and create substantial artifacts (e.g., gaps in the image). Certain ferromagnetic materials, for example, may not be suitable because they may create artifacts in an MRI image. The occlusive implants 10, 110 and/or the embolization device 150 may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the occlusive implants 10, 110 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implants 10, 110 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive implant, comprising:
   an expandable framework configured to shift between a collapsed configuration and an expanded configuration; and
   an occlusive member disposed along at least a portion of the expandable framework;
   a first negatively charged coating, wherein at least part of the occlusive implant is adapted to repel fibrinogen,
   a second positively charged coating, wherein at least part of the occlusive implant is adapted to attract fibrinogen,
   wherein a portion of the occlusive member is between the first coating and the second coating.

2. The occlusive implant of claim 1, wherein the occlusive implant has a leading edge, and an area of the occlusive member proximate the leading edge is treated to repel fibrinogen.

3. The occlusive implant of claim 1, wherein the expandable framework includes a central structure, and an area of the occlusive member proximate the central structure is treated to repel fibrinogen.

4. The occlusive implant of claim 1, wherein at least part of the occlusive implant is configured to carry a negative charge at neutral pH.

5. The occlusive implant of claim 1, wherein at least part of the occlusive implant includes a polymer that is negatively charged as a consequence of exposure to neutral pH.

6. The occlusive implant of claim 5, wherein the polymer that is negatively charged at neutral pH covers at least part of the occlusive member.

7. The occlusive implant of claim 5, wherein the polymer that is negatively charged at neutral pH is spray coated onto the occlusive member.

8. The occlusive implant of claim 5, wherein the polymer that is negatively charged at neutral pH is physically blended with a material forming the occlusive member.

9. The occlusive implant of claim 5, wherein the polymer that is negatively charged at neutral pH is provided as a copolymer with a material forming the occlusive member.

10. The occlusive implant of claim 1, wherein the positively charged coating is polymeric and covers at least a portion of the expandable framework.

11. The occlusive implant of claim 1, wherein the occlusive member is formed of polyethylene terephthalate (PET).

12. The occlusive implant of claim 1, wherein the expandable framework includes a plurality of anchor members extending radially outward from the expandable framework.

13. The occlusive implant of claim 12, wherein the expandable framework and the plurality of anchor members are formed from a unitary tubular member.

14. The occlusive implant of claim 1, wherein the expandable framework, in the expanded configuration, is configured to fit into a left atrial appendage (LAA) of a patient's heart.

15. The occlusive implant of claim 1, wherein a second part of the occlusive implant not configured to repel fibrinogen is configured to attract fibrinogen.

16. A medical implant adapted to occlude a left atrial appendage (LAA) of a patient's heart, the medical implant comprising:
   an expandable framework configured to shift between a collapsed configuration and an expanded configuration;
   an occlusive member extending over and supported by at least a portion of the expandable framework; and
   a first negatively charged coating that is configured to repel fibrinogen, the first coating disposed over at least part of the occlusive member,
   a second positively charged coating that is configured to attract fibrinogen, the second coating disposed over at least part of the occlusive member,
   wherein a portion of the occlusive member is between the first coating and the second coating.

17. The medical implant of claim 16, wherein the first coating that is configured to repel fibrinogen comprises a polymer that is negatively charged as a consequence of exposure to neutral pH.

18. The medical implant of claim 16, wherein the occlusive implant has a leading edge, and the first coating that is configured to repel fibrinogen extends over the leading edge.

19. The medical implant of claim 16, wherein the expandable framework includes a central structure, and the first coating that is configured to repel fibrinogen extends over the central structure.

20. A medical implant adapted to occlude a left atrial appendage (LAA) of a patient's heart, the medical implant comprising:
   an expandable framework configured to shift between a collapsed configuration and an expanded configuration;
   an occlusive member extending over and supported by at least a portion of the expandable framework;
   a first negatively charged coating disposed over a first part of the occlusive member, the first coating being configured to repel fibrinogen; and
   a second positively charged coating disposed over a second part of the occlusive member, the second coating being configured to attract fibrinogen;
   wherein a portion of the occlusive member is between the first coating and the second coating.

* * * * *